United States Patent [19]
Tinti et al.

[11] Patent Number: 4,812,478
[45] Date of Patent: Mar. 14, 1989

[54] DERIVATIVES OF L-AMINO ACYL L-CARNITINE, PROCESS FOR THEIR PREPARATION AND PHARMACEUTICAL COMPOSITIONS HAVING HEPATOPROTECTING ACTIVITY CONTAINING SAME

[75] Inventors: Maria O. Tinti; Carlo A. Bagolini; Domenico Misiti, all of Rome; Carlo Scolastico, Milan, all of Italy

[73] Assignee: Sigma-Tau Industrie Farmaceutiche Riunite S.p.A., Rome, Italy

[21] Appl. No.: 67,694

[22] Filed: Jun. 29, 1987

[30] Foreign Application Priority Data

Jul. 2, 1986 [IT] Italy ................................ 48217 A86

[51] Int. Cl.$^4$ .................... C07C 149/243; A61K 31/22
[52] U.S. Cl. ..................................... 514/550; 514/551; 560/147; 560/155; 560/168
[58] Field of Search ............... 560/147, 159, 155, 168; 514/550, 551

[56] References Cited

U.S. PATENT DOCUMENTS

| | | | |
|---|---|---|---|
| 4,401,827 | 8/1983 | Witt | 560/1 |
| 4,663,352 | 5/1987 | Onofrj | 514/556 |

FOREIGN PATENT DOCUMENTS

| | | |
|---|---|---|
| 150688 | 8/1985 | European Pat. Off. |
| 2077258 | 12/1981 | United Kingdom |

OTHER PUBLICATIONS

Comber, Org. Prep. Proc., Int., 17 pp. 175–181, (1985).
Mromie, "Protective Groups in Organic Chemistry," pp. 43, 44 55–60, 183–185, 196–198 (1973).
Fieser, "Reagents for Organic Synthesis," vol. 1, pp. 114–116 (1967).
Staab, Ber., 95 pp. 1284–1297 (1962).

Primary Examiner—Michael L. Shippen
Attorney, Agent, or Firm—Ladas & Parry

[57] ABSTRACT

L-aminoacyl derivatives of L-carnitine of general formula (I)

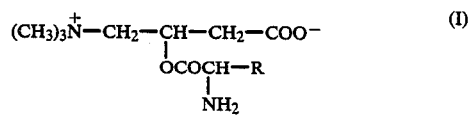

wherein R is an alkyl radical selected from 1-methylpropyl, isobutyl, isopropyl, mercaptomethyl and 3-guanidino propyl, and their pharmacologically acceptable salts, are prepared e.g. by reacting a solution in an organic solvent of L-carnitine whose carboxyl group is protected with an N-protected aminoacid in the presence of a condensing agent and then removing the aminoacid and carnitine protecting groups, thus obtaining the desired compound.

12 Claims, No Drawings

DERIVATIVES OF L-AMINO ACYL L-CARNITINE, PROCESS FOR THEIR PREPARATION AND PHARMACEUTICAL COMPOSITIONS HAVING HEPATOPROTECTING ACTIVITY CONTAINING SAME

The present invention relates to a novel class of L-amino acyl L-carnitines, the process for their preparation and the pharmaceutical compositions having hepatoprotecting activity comprising these compounds as active principles.

More particularly, the present invention relates to L-amino acyl-carnitines of general formula (I)

$$(CH_3)_3\overset{+}{N}-CH_2-CH-CH_2-COO^- \quad (I)$$
$$| \quad OCOCH-R$$
$$| \quad NH_2$$

wherein R is an alkyl radical selected from 1-methylpropyl, isobutyl, isopropyl, mercaptomethyl and 3-guanidino propyl, and their pharmacologically acceptable salts.

Therefore, if the meanings of R are taken into account, the compounds specifically encompassed by the general formula (I) are:

(a) L-isoleucyl L-carnitine:

$$(CH_3)_3\overset{+}{N}CH_2CHCH_2COO^-$$
$$| \quad CH_3$$
$$OCOCHCHCH_2CH_3$$
$$| \quad NH_2$$

(b) L-leucyl L-carnitine:

$$(CH_3)_3\overset{+}{N}CH_2CHCH_2COO^-$$
$$| \quad OCOCHCH_2CH(CH_3)_2$$
$$| \quad NH_2$$

(c) L-valyl L-carnitine:

$$(CH_3)_3\overset{+}{N}CH_2CHCH_2COO^-$$
$$| \quad OCOCHCH(CH_3)_2$$
$$| \quad NH_2$$

(d) L-cysteinyl L-carnitine:

$$(CH_3)_3\overset{+}{N}CH_2CHCH_2COO^-$$
$$| \quad OCOCHCH_2SH$$
$$| \quad NH_2$$

(e) L-arginyl L-carnitine:

$$(CH_3)_3\overset{+}{N}CH_2CHCH_2COO^- \quad NH$$
$$| \quad \qquad\qquad\qquad\qquad ||$$
$$OCOCH(CH_2)_3NHCNH_2$$
$$| \quad NH_2$$

It is apparent that the pharmacologically acceptable salts of the compounds of formula (I) may have the general formula (I')

$$(CH_3)_3\overset{+}{N}CH_2CHCH_2COOH \quad (I')$$
$$| \quad OCOCHR$$
$$X^- \quad | \quad NH_2$$

wherein $X^-$ is the anion of a pharmacologically acceptable acid, such as for instance hydrochloric, bromidric, phosphoric, sulphuric and orotic acid; or they may have the general formula (I'')

$$(CH_3)_3\overset{+}{N}CH_2CHCH_2COOH \quad (I'')$$
$$| \quad OCOCHR$$
$$X^- \quad | \quad +NH_3X^-$$

wherein $X^-$ has the above-identified meaning.

Since the salts (I'') are more stable than both the salts (I') and the inner salts (I) and since in every case the conversion from the (I'') or (I') salts into inner salts is carried out via known procedures (using e.g. ionic exchange resins whose selection will be obvious to any average skilled expert) for simplicity sake reference will be made hereinbelow to the salts of formula (I'').

Acyl derivatives of L-carnitine are already known. These acyl derivatives of L-carnitine are prepared by dissolving L-carnitine in trifluoroacetic acid and treating the resulting solution with the acid chloride of the desired acid. This synthesis route cannot be used for preparing the L-aminoacyl derivatives of L-carnitine of the present invention because:

(1) the activation of an aminoacid as acid chloride is only feasible upon previous protection of the $NH_2$ group with suitable protecting groups (e.g. acetyl and tosyl) whose subsequent removal requires such reaction conditions as to break the ester bond and/or lead to formation of unsaturated by-products, such as crotonoyl-betaine;

(2) the use of trifluoro acetic acid (the carnitine solvent of choice) brings about the instability and poor reactivity of the acid chloride of the protected aminoacid.

According to the present invention, the above-identified problems are overcome:

(1') by using N,N'-carbonyldiimidazole as activator of the aminoacid carboxyl group;

(2') by using, in place of trifluoroacetic acid, an inert organic solvent wherein, however, carnitine would be unsoluble.

In accordance with the present invention, this latter problem is solved by following either one of these alternatives routes:

(a) either synthesizing an ester of a carnitine salt which is soluble in the desired organic solvent and easily hydrolyzable after condensation with the amino acid for restoring the free carboxyl group; or (b) using an L-carnitine precursor soluble in the desired organic solvent and subsequently converting the aminoacyl derivative of the precursor into L-carnitine aminoacyl derivative.

In accordance with the present invention, the L-amino acyl derivatives of L-carnitine of formula (I) are, therefore, prepared via two distinct synthesis routes depending on whether as starting material either the ester of an L-carnitine salt is used, preferably benzyl L-carnitine perchlorate (process A) or L- or D,L-norcarnitine tert-butyl ester (process B).

Specifically, process A comprises the following steps:

(a) reacting at 0° C.–30° C., for 0.5–24 hours, a benzyl L-carnitine salified with an anion y⁻ selected from perchlorate, tetraphenylborate and iodide in an inert anhydrous organic solvent selected from tetrahydrofurane and acetonitrile, with an L-aminoacid having its NH₂ group protected as N-carbobenzoxy, in the presence of N,N′-carbonyldiimidazole;

(b) substituting the anion X⁻ for the anion y⁻ by means of a weakly basic ion exchange resin by eluting the product in an alcoholic or aqueous-alcoholic solvent;

(c) removing the N-carbobenzoxy group of the aminoacid and the benzyl radical of benzyl L-carnitine by hydrogenation in the presence of a hydrogenation catalyst selected from 10% Pd/C and PtO₂ is an alcoholic, aqueous-alcoholic solvent or water at room temperature at a pressure of 1–4 kg/cm².

Preferably, the ion exchange resin of step (b) is AMBERLYST A21 resin (macroreticular ion exchange resin with a styrene divinyl benzene polymer backbone, weakly basic, tertiary amine) activated in Cl⁻ form.

Process B comprises the following steps:

(a') reacting at 0° C.–30° C., for 4–24 hours L- or D,L-norcarnitine tert-butyl ester in a solvent selected from tetrahydrofurane and acetonitrile with an L-aminoacid having its NH₂ group protected as N-carbotertbutoxy in the presence of N,N′-carbonyl diimidazole;

(b') in the event D,L-norcarnitine tert-butylester has been used, separating the two diastereoisomers thus formed, L-N-carbotertbutoxy aminoacyl L-norcarnitine tertbutyl ester and L-N-carbotertbutoxy amino acyl D-norcarnitine tert butyl ester, via known procedures;

(c') methylating at 15° C.–30° C., for 4–24 hours the product obtained in step (a') or (b') with methyl iodide in an organic solvent selected from acetone and methyl ethyl ketone;

(d') removing the N-carbotertbutoxy group of the aminoacid and the tert-butyl radical in an acid environment, using trifluoroacetic acid or a gaseous HCl solution in an inert solvent selected from chloroform and methylene chloride; and (e') substituting the X⁻ anion for the I⁻ anion eluting an aqueous or alcoholic solution of the product of step (d') on a weakly basic ion exchange resin.

Preferably, the separation of step (b') is carried out either by chromatography on a silica column or by preparative HPLC.

Processes A and B are illustrated in the following reaction scheme.

Process A

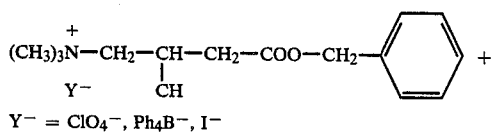

Y⁻ = ClO₄⁻, Ph₄B⁻, I⁻

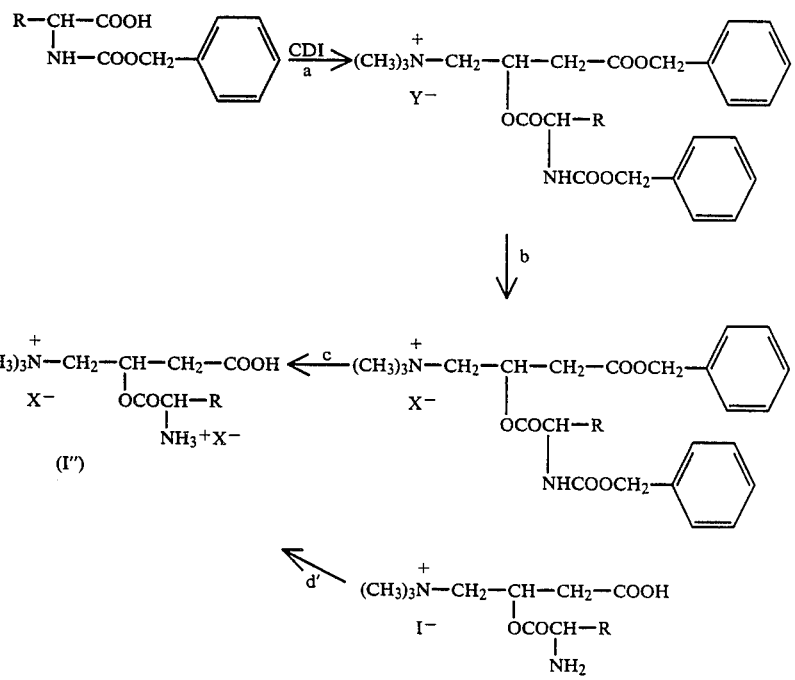

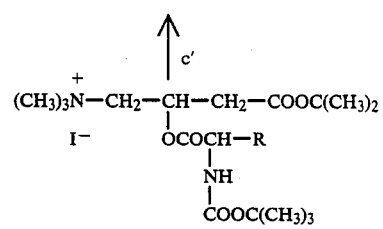

Process B

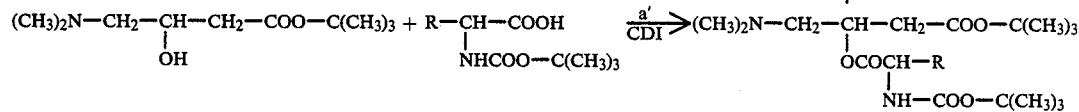

The following non-limiting examples illustrate the preparation of some of the compounds of the present invention.

EXAMPLE 1

Preparation of L-leucyl L-carnitine chloride hydrochloride (ST 599) ((Process A)

(a) Preparation of N-carbobenzoxy L-leucyl L-carnitine benzyl ester perchlorate

N-carbobenzoxy L-leucine (2.65 g; 0.01 moles) was dissolved in 10 cc of anhydrous tetrahydrofurane (THF). N,N'-carbonyl diimidazole (1.82 g; 0.012 moles) at 0° C. was added to the solution. The resulting solution was kept under stirring at room temperature for half an hour. Then, a solution of L-carnitine benzyl ester perchlorate (3.5 g; 0.01 moles) in 5 cc of anydrous THF was added. The mixture was kept at room temperature for 24 hours. To the filtered reaction mixture 10 cc of 10% $Na_2CO_3$ were added. The solid thus formed was filtered off and the filtrate was diluted with 10 cc $H_2O$ and twice extracted with ethyl acetate. The organic phase was washed with 10 cc $H_2O$, dried over $Na_2SO_4$ and brought to dryness.

The oily residue thus obtained was dissolved in chloroform and washed with $H_2O$. The chloroform concentrate yielded a residue of 3.3 g (yield about 55%). The product was examined via HPLC.

| Column | Bondapak $C_{18}$ |
|---|---|
| Eluant | $NH_4H_2PO_4$ 0.05M—$CH_3CN$ 60-40 |
| Pressure | 57 atm (58.881 kg/cm$^2$) |
| Flow rate | 2 ml/min |
| Detector | UV λ 205 |
| Chart speed | 0.5 cm/min |
| Rt | 17.66 minutes |

(b) Preparation of N-carbobenzoxy L-leucyl L-carnitine benzyl ester chloride

N-carbobenzoxy L-leucyl L-carnitine benzylester perchlorate (3 g; 0,005 moles) was dissolved in methanol and the resulting solution passed through a column of 30 ml of AMBERLYST A21 resin (macroreticular ion exchange resin with a styrene divinyl benzene polymer backbone, weakly basic, tertiary amine) activated in Cl$^-$ form. The resin was eluted with methanol. The concentrated methanol solution yielded 2.5 g of a hydroscopic white solid (yield 95%).

(c) Removal of the protecting groups of N-carbobenzoxy L-leucyl L-carnitine benzylester chloride N-carbobenzoxy L-leucyl L-carnitine benzyl ester chloride (2.5 g; 0,0047 moles) was dissolved in 25 cc $H_2O$ and hydrogenated with 0.5 g of 10% Pd/C under pressure (40 psi; 2.8 kg/cm$^2$) at room temperature for 4 hours. The solution was filtered and 0.5 g of 10% Pd/C added to it; the hydrogenation was continued for 24 hours. At the end of the hydrogenation the aqueous solution was filtered and lyophilized. 1.2 g of a hygroscopic white solid were obtained (yield 80%). The product thus obtained was purified by preparative HPLC.

| Chromatograph | Water Delta prep. 3000 |
|---|---|
| Column | Prepak $C_{18}$ |
| Detector | R.I. Iota |
| Recorder | Houston "Omniscribe" |
| Eluant | $H_2O$ 100% |
| Flow rate | 20 ml/min |
| Column pressure | 750 psi (52.7 kg/cm$^2$) |
| Eluant pressure | 40 psi (2.8 kg/cm$^2$) |

1 g of the product was dissolved in 20 ml $H_2O$. The solution was filtered on W42 filter and injected into the chromatograph. The collected fractions were acidified and lyophilized; 350 mg of the title product were obtained (yield 35%). The lyophilized product, washed with ethyl ether and dried, had the following analytical characteristics:

$[\alpha]_{25}^{D} = -6.6 (C=1, H_2O)$.

Melting point=190° C. dec. (it softens at 110° C).

TLC=$CHCl_3$, MetOH, $NH_4OH$; 50, 30, 8

Rf=0.1, $I_2$ detector

K.F.=2.5% Elementary analysis: for $C_{13}H_{28}N_2O_4Cl_2$; C 43.49%; H 9.76%; N 7.95%; Cl 20.59%.

NMR $D_2O$ 5.9 (1H, m

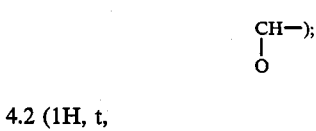

4.2 (1H, t,

3.8 (2H, m, N+—CH$_2$—); 3.3 (9H, s, (CH$_3$)$_3$N+); 3.0 52H, d, —CH —COOH); 2.2–1.8 (3H, m, C$\underline{H}_2$—C$\underline{H}$); 1.0 (6H, d, CH—(C$\underline{H}_3$)$_2$).

EXAMPLE 2

Preparation of L-valyl L-carnitine chloride hydrochloride (ST 601) (Process A)

(a) Preparation of N-carbobenzoxy L-valyl L-carnitine benzyl ester perchlorate

N-carbobenzoxy L-valine (34 g; 0.13 moles) was dissolved in 130 cc of anhydrous THF. N,N'-carbonyl diimidazole (25 g; 0.15 moles) was added to the solution. The solution was kept under stirring at 0° C. for 30 minutes. Then, a solution of L-carnitine benzyl ester perchlorate (45 g; 0.13 moles) in 65 cc THF was added and the resulting solution was kept under stirring at room temperature for 24 hours. 130 cc of 10% Na$_2$CO$_3$ were then added to the solution. After the solid thus formed was filtered off, the filtrate diluted with 150 cc H$_2$O was twice extracted with 150 cc of ethyl acetate. The organic phase dried over anhydrous Na$_2$SO$_4$ was concentrated under vacuum. The oily residue was dissolved in CH$_2$Cl$_2$ and washed with H$_2$O. The dried organic phase was concentrated to dryness yielding 52 g of a hygroscopic solid (yield 68%).

| | |
|---|---|
| TLC CHCl$_3$ 50, CH$_3$OH 30, NH$_4$OH 8 | |
| Rf = 0.9 | |
| HPLC | |
| Column | μ Bondapak C$_{18}$ |
| Eluant | NH$_4$H$_2$PO$_4$ 0.05M—CH$_3$CN 60-40 |
| Pressure | 46 atm (47.518 kg/cm$^2$) |
| Flow rate | 1 ml/min |
| Detector | UV λ = 205; att. 4 |
| Chart speed | 0.5 cm/min |
| Rt | 23.99 min |

(b) Preparation of N-carbobenzoxy L-valyl L-carnitine benzyl ester chloride

N-carbobenzoxy L-valyl L-carnitine benzyl ester perchlorate (52 g) was dissolved in 200 cc methanol and the resulting solution eluted through a column of 600 ml of AMBERLYST A21 resin (macroreticular ion exchange resin with a styrene divinyl benzene polymer backbone, weakly basic, tertiary amine) activated in Cl$^-$ form. The eluate was concentrated under vacuum, thus obtaining 46 g of N-carbobenzoxy L-valyl L-carnitine benzyl ester chloride (yield 100%).

(c) Conversion of N-carbobenzoxy L-valyl L-carnitine benzyl ester chloride into L-valyl L-carnitine chloride hydrochloride N-carbobenzoxy L-valyl L-carnitine benzyl ester chloride (46 g; 0.088 moles) was dissolved in 100 cc H$_2$O. 10 g of 10% Pd/C were added to the solution. The resulting reaction mixture was hydrogenated under pressure (24 psi; 1.68 kg/cm$^2$) for 4 hours. Subsequently, further 10 g of catalyst were added to the reaction mixture and the hydrogenation was continued for 20 hours at 50 psi (3.51 kg/cm$^2$); the solution was filtered and lyophilized. 23 g of the of the title compound were obtained (yield 88%). The compound was purified by preparative HPLC.

| | |
|---|---|
| Chromatograph | Water delta prep. 3000 |
| Column | Prepak C$_{18}$ |
| Detector | R.I. Iota |
| Recorder | Houston "Omniscribe" |
| Eluant | H$_2$O 100% |
| Flow rate | 20 ml/min |
| Column pressure | 750 psi (52.7 kg/cm$^2$) |
| Eluant pressure | 40 psi (2.81 kg/cm$^2$) |

1 g sample was dissolved in 20 ml H$_2$O, the solution filtered on W 42 filter and injected into the chromatograph.

The collected fractions were acidified with 1N HCl 400 mg of the title compound were obtained.

| HPLC | |
|---|---|
| Column | μ Bondapak NH$_2$ |
| Pressure | 1000 psi (70.31 kg/cm$^2$) |
| Flow rate | 1 ml/min |
| Eluant | KH$_2$PO$_4$ 0.05N—CH$_3$CN (35-65) |
| UV Detector | λ 205; att.30 |
| Chart speed | 0.5 cm/min |
| Rt | 23.7 minutes |

NMR D$_2$O δ5.8 (1H, m,

4.3 (1H, d, —CH—NH$_2$); 4.0 (2H, m, N+—CH$_2$); 3.4 (9H, s, (CH$_3$)$_3$N+); 2.9 (2H, d, C$\underline{H}_2$—COOH); 2.4–2.2 (1H, m, CO—CH—); 1.2 (6H, d, C$\underline{H}$(CH$_3$)$_2$.

[α]$_{25}^D$ = −7.45 (c=1 H$_2$O).

Melting point=160° C. dec (it softens at 110° C).

TLC=CHCl$_3$, MetOH, NH$_4$OH; 50, 30, 8.

R$_F$=0.3; rivelatore I$_2$

K.F. =6.5%

Elementary analysis: for C$_{12}$H$_{26}$N$_2$O$_4$Cl$_2$: C 40.78%; H 8.15%; N 8.03%; Cl 18.91.

EXAMPLE 3

Preparation of L-isoleucyl L-carnitine chloride (ST 583) (Process B)

(a') Preparation of N-carbotertbutoxy L-isoleucyl D,L-norcarni tine tert-butylester N,N'-carbonyl diimidazole (2.7 g; 0.017 moles) was added at 0° C. to a solution of N-carbotertbutoxy L-isoleucine (2.4 g; 0.01 moles) in 10 cc anhydrous THF. To this solution kept under stirring at room temperature for 30 minutes under a nitrogen atmosphere, D,L-norcarnitine tert-butyl ester (2.03 g; 0.01 moles) dissolved in 5 cc THF was then added. This mixture was kept at room temperature for 24 hours. 10 cc of 10% Na$_2$CO$_3$ were then added.

The resulting mixture was kept under stirring for 30 minutes and then filtered. The aqueous solution diluted with 10 cc H$_2$O was twice extracted with 10 cc ethyl acetate. The organic phase, washed with H$_2$O, was concentrated under vacuum. An oil was obtained which washed with cyclohexane gave 2.3 g of a product. This product, examined by TLC (AcOEt 98-triethylamine 2, development ninidrine), showed two spots at Rf 0.77 and 0.84 corresponding to the two diasterisomers thus formed. The raw reaction product was subjected to preparative HPLC. The compound at lower Rf was isolated, corresponding to N-carbotertbutoxy L-isoleucyl L-norcarnitine tert-butyl ester (yield about 60%).

| Chromatograph | Jobin Yvon; prep. 100 with SS column of 4 cm of diameter |
|---|---|
| Detector | KNAVER X 16 refractometer |
| Recorder | Houston Omniscribe |
| Resin | Lichropre SI 60 15-25 g 200 |
| Eluant | ethyl acetate: 45%; chloroform: 55% |
| Column pressure | 12 atm (12.396 kg/cm$^2$) |
| Eluant pressure | 6 atm (6.198 kg/cm$^2$) |
| Flow rate | 30 ml/min |

NMR CHCl$_3$ δ5.4 (1H, m,

5.0 (1H, d, —NH—); 4.2 (1H, m, —CH—NH—); 3.8 (2H, d, N+—CH$_2$); 2.5-2.2 (2H, m, —CH$_2$—COO+6H, s, (CH$_3$)$_2$N); 1.8-1.2 (3H, m, CH—CH$_2$CH$_3$+18H, s, 2(CH$_3$)$_3$); 1.9 (6H, d,

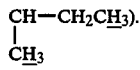

(b') Preparation of N-carboterbutoxy L-isoleucyl L-carnitine tert-butyl ester iodide 15 cc methyl iodide were added to a solution of N-carbotertbutoxy L-isoleucyl L-norcarnitine tert-butyl ester (22 g; 0.053 moles) in 220 cc acetone. The solution was kept at room temperature for 4 hours and then concentrated to dryness under vacuum. 29 g of product (0.052 moles; yield 100%) were obtained.

TLC: CHCl$_3$, 50; MetOH, 30; NH$_4$OH, 8; Rf, 0.8.
NMR CDCl$_3$ δ5.6(1H, m,

4.9 (1H, d, —NH—); 4.3-3.8 (3H, m,

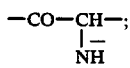

—CH$_2$N$^{30}$ ); 3.5 (9H, s, (CH$_3$)$_3$N+); 2.0 (2H, d, CH—COOH); 1.8-1.3 (18H, s, —COOC(CH$_3$)$_3$; NHCOOC(CH$_3$)$_3$+3H, m, CH—CH—CH$_2$—; CH$_2$CH$_3$); 1.0 (6H, m,

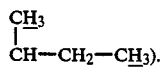

(c') and (d') Conversion of N-carbotertbutoxy L-isoleucyl L-carnitine tert-butyl ester iodide into L-isoleucyl L-carnitine chloride N-carbotertbutoxy L-isoleucyl L-carnitine tert-butyl ester iodide (29 g; 0.052 moles) was dissolved in 96 cc trifluoroacetic acid and the solution kept under stirring at 0° C. for 2 hours. Ethyl ether was added to the solution until a yellow oil precipitated. The resulting suspension was decanted, the precipitate dissolved in H$_2$O and the aqueous solution was extracted with ethyl ether three times. The aqueous solution was decolorized with active charcoal, filtered and eluted through a column of IR 45 AMBERLITE resin activated in Cl$^-$ form. The eluate was lyophilized and 12 g (yield 66%) of products were obtained.

TLC: CHCl$_3$, 50; MetOH, 30; NH$_4$OH, 8; Rf=0.3.
The product was further purified via preparative HPLC.

| Chromatograph | Jobin Yvon prep. 100 with SS column of 4 cm of diameter. |
|---|---|
| Detector | R.I. Knaver X 16 |
| Recorder | HOUSTON "OMNISCRIBE" 0.5 cm/min |
| Resin | Lichroprep RP$_{18}$ 25-40 m 200 g |
| Eluant | H$_2$O 100% |
| Column pressure | 10 atm (10.33 kg/cm$^2$) |
| Eluant pressure | 3 atm (3.099 kg/cm$^2$) |
| Flow rate | 28 ml/min |
| 6 g of pure product were obtained. | |

NMR D$_2$O δ5.7 (1H, m, $$-CH-\atop|\atop O-$$

4.2-3.8 (3H, m, $$CO-CH\atop|\atop NH_2$$

CH$_2$—N+); 3.2 (9H, s, (CH$_3$)$_3$N+); 2.7 (2H, d, CH$_2$—COOH); 2.1 (1H, m, $$-CH-\atop|\atop CH_3$$

1.3 (2H, t, CH$_2$CH$_3$); 0.9 (6H, m, $$-CH-CH_2-CH_3)\atop|\atop CH_3$$

| HPLC | Varian |
|---|---|
| Column | μ Bondapack NH$_2$ |
| Eluant | KH$_2$PO$_4$ 0.05N—CH$_3$CN (35-65); flow rate 1 ml/min |
| Detector | UV LC 75; λ 205; att. 4 |
| Integrator | 4270 Varian |
| Chart speed | 0.5 cm/min |
| Rt | 18.65 minutes |

[α]$_{25}^D$= +1.8 (c=1, H$_2$O).
Melting point=129° C. dec.
K. F.=6.8%
Elementary analysis: for C$_{13}$H$_{27}$N$_2$O$_4$Cl: C 47.90%; H 8.98%; N 8.84%; Cl 11.49%.

EXAMPLE 4

Preparation of L-arginyl L-carnitine chloride hydrochloride (Process A)

(a) Preparation of $N_\alpha$, $N_\delta$, $N_\omega$-tricarbobenzoxy L-arginyl L-carnitine benzyl ester perchlorate $N_\alpha$, $N_\delta$, $N_\omega$-tricarbobenzoxy L-arginine (57.6 g; 0.1 moles) was dissolved in 100 cc anhydrous THF. To the solution, N,N'-carbonyl diimidazole (15 g; 0.11 moles) was added. The solution was kept under stirring at room temeprature for 45 minutes. Then, dimethyl amino-pyridine (1.2 g; 0.01 moles) and a solution of L-carnitine benzyl ester perchlorate (35 g; 0.1 moles) in 50 cc THF were added. The resulting solution was kept under stirring at room temperature for 48 hours and then concentrated under vacuum. The residue was dissolved in $CH_2Cl_2$ and washed with 1% HCl. The organic phase was dried over anhydrous $Na_2SO_4$ and concentrated under vacuum. 73 g of a hygroscopic solid (yield 80%) were obtained.

| HPLC | |
|---|---|
| Column | Lichrosorb RP-8 |
| Eluant | $KH_2PO_4$ 0.05M—$CH_3CN$ 40-60 |
| Pressure | 57 atm (58.881 kg/cm$^2$) |
| Flow rate | 1 ml/min |
| Detector | UV λ 205 |
| Chart speed | 0.5 cm/min |
| Rt | 11.07 minutes |

(b) Preparation of $N_\alpha$, $N_\delta$, $N_\omega$-tricarbobenzoxy L-arginyl L-carnitine benzyl ester chloride $N_\alpha$, $N_\delta$, $N_\omega$-tricarbobenzoxy L-arginyl L-carnitine benzylester perchlorate (75 g; 0.08 moles) was dissolved in methanol and the resulting solution fed at the top of a column containing 750 ml of AMBERLYST A21 resin (macroreticular ion exchange resin with a styrene divinyl benzene polymer backbone, weakly basic, tertiary amine) activated in Cl$^-$ form. The resin was eluted with methanol. The concentrated methanol solution yielded 68 g of a hygroscopic white solid (yield 95%). The product thus obtained was purified via preparative HPLC.

| Chromatograph: | waters Delta prep 3000 |
|---|---|
| Column | Prepak $C_{18}$ a 750 psi |
| Eluant | $CH_3CN$ 70: $H_2O$ 30 |
| Flow rate | 30 ml/min |

2 g of product were dissolved in 20 ml $CH_3CN$, filtered through a W 42 filter and injected into the chromatograph. The collected fractions were concentrated under vacuum and subjected to HPLC examination at the same conditions outlined at point (a).

The fractions with $R_t = 10.86$ were combined and 32 g (yield 47%) of pure product were obtained.

(c) Removal of protecting groups from $N_\alpha$, $N_\delta$, $N_\omega$-tricarbobenzoxy L-arginyl L-carnitine benzyl ester chloride $N_\alpha$, $N_\delta$, $N_\omega$,-tricarbobenzoxy L-arginyl L-carnitine benzyl ester chloride (4.2 g; 0.005 moles) was dissolved in 50 cc $H_2O$. 1.5 cc concentrated HCl were added to the solution. The resulting solution was hydrogenated with 1 g of 10% Pd/C under pressure (40 psi; 2.8 kg/cm$^2$) at room temperature for 24 hours. The reaction mixture was filtered and 1 g of 1% Pd/C were added to the filtrate; the hydrogenation was continued for 24 hours.

When the hydrogenation ended, the reaction mixture was filtered and the filtrate was lyophilized. 2 g of a hygroscopic white solid were obtained (yield 86%). The product thus obtained was purified via preparative HPLC.

| Chromatograph | Waters delta prep. 3000 |
|---|---|
| Column | Prepak $C_{18}$ |
| Detector | R.I. Iota |
| Recorder | Houston "Omniscribe" |
| Eluant | $H_2O$ 100% |
| Flow rate | 20 ml/min |
| Column pressure | 750 psi (52.7 kg/cm$^2$) |
| Eluant pressure | 40 psi (2.8 kg/cm$^2$) |

1 g of the product was dissolved in 20 ml $H_2O$, the solution filtered through W 42 filter and injected into the chromatograph. The collected fractions were acidified and lyophilized; 500 mg of the title product were obtained (yield 35%). The lyophilized product, washed with ethyl ether and dried, showed the following analytical characteristics:

$[\alpha]_{25}^D = -6.6$ (C=1, $H_2O$).

TLC=$CHCl_3$, MetOH, $NH_4OH$; 50, 30, 8.

$R_F=0.1$, $I_2$ detector. NMR=$D_2O$ δ5.7 (1H, m,

); 4.3 (1H, m,

);

3.8 (2H, m, $N^+CH_2$—) 3.3 (11H, S, $5CH_3)_3N^+$—, $CH_2$—NH); 2.8 (2H, d, —$CH_2COOH$); 1.8 (4H, m, —$CH_2$—$CH_2$—).

The hepatoprotecting activity of the compounds was evaluated towards ethionine- and ammonium acetate-induced intoxication. It was found that the compounds are active both orally and parenterally at a dose equal to or lower than 10 mg/kg. Moreover, in vitro tests have shown that they are able to keep the structural and functional integrity of liver cells and mitochondria towards hexogenous noxae at nanomolar and micromolar concentrations.

Following single or repeated administrations for 15 days the compounds did not induce any toxic or lethal effect up to a dose of 1 g/kg orally or parenterally.

These compounds are, therefore, active for the therapeutical treatment of hepatic diseases which severely impair liver function.

The orally or parenterally administrable compositions which contain one of compounds of the present invention as active principle (e.g. tablets, capsules and injectable vials) are compounded with the usual excipients via procedures well known to the average skilled expert in pharmaceutical technology.

What is claimed is:

1. L-aminoacyl L-carnitine of the formula (I)

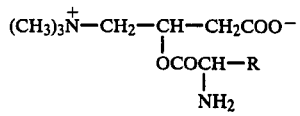

wherein R is an alkyl radical selected from mercaptomethyl and 3-guanidinopropyl, and their pharmacologically acceptable salts.

2. Pharmacologically acceptable salts of L-amino acyl L-carnitine having the general formula (I')

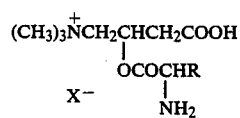

wherein R is an alkyl radical selected from the group consisting of mercaptomethyl and 3-guanidinopropyl and their pharmacologically acceptable salts and X is the anion of a pharmacologically acceptable acid selected from the group consisting of hydrochloric, bromidic, phosphoric, sulphuric and orotic acid.

3. Pharmacologically acceptable salts of L-amino acyl L-carnitine having the formula (I")

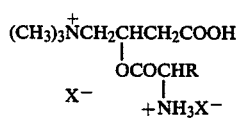

wherein R is an alkyl radical selected from the group consisting of mercaptomethyl and 3-guanidinopropyl and their pharmacologically acceptable salts and X is the anion of a pharmacologically acceptable acid selected from the group consisting of hydrochloric, bromidic, phosphoric, sulphuric and orotic acid.

4. A process for producing pharmacologically acceptable salts of L-aminoacyl L-carnitines of the formula (I")

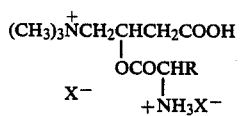

wherein R is an alkyl radical selected from the group consisting of 1-methyl-propyl, isobutyl, isopropyl, mercaptomethyl and 3-guanidinopropyl and their pharmacologically acceptable salts and X is the anion of a pharmacologically acceptable acid selected from the group consisting of hydrochloric, bromidic, phosphoric, sulphuric and orotic acid which comprises the following steps:

(a) reacting at 0° C.-30° C. for 0.5-24 hours, a benzyl L-carnitine salified with an anion $y^-$ selected from perchlorate, tetraphenylborate and iodide in an inert anhydrous organic solvent selected from tetrahydrofurane and acetonitrile, with an L-amino acid having its $NH_2$ group protected as N-carbobenzoxy, in the presence of N,N'-carbonyldiimidazole;

(b) substituting for the anion $y^-$ the anion $X^-$ from a weakly basic ion exchange resin by eluting the product in an alcoholic or aqueous-alcoholic solvent;

(c) removing the N-carbobenzoxy group of the aminoacid and the benzyl radical of benzyl L-carnitine by hydrogenation in the presence of a hydrogenation catalyst selected from 10% Pd/C and $PtO_2$ in an alcoholic, aqueous-alcoholic solvent or water at room temperature at a pressure of 1–4 $kg/cm^2$.

5. A process for producing pharmacologically acceptable salts of L-amino L-carnitines halogenides of The formula (I')

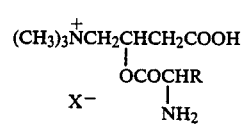

wherein $X^-$ is anion of a pharmacologically acceptable acid selected from the group consisting of hydrochloric, bromidic, phosphoric, sulphuric and orotic acid and R is an alkyl radical selected from the group consisting of 1-methyl-propyl, isobutyl, isopropyl, mercaptomethyl and 3-guanidinopropyl and their pharmacologically acceptable salts, comprising the following steps:

(a') reacting at 0° C.-30° C., for 4–24 hours L- or D, L-norcarnitine tert-butyl ester in a solvent selected from tetrahydrofurane and acetonitrile with an L-aminoacid having its $NH_2$ group protected as N-carbotertbutoxy in the presence of N,N'-carbonyldiimidazole;

(b') in the event wherein D, L-norcarnitine tert-butyl ester has been used, separating the two diastereoisomers thus formed, L-N-carbotertbutoxy aminoacyl L-norcarnitine tert butyl ester and L-N-carboterbutoxy amino acyl D-norcarnitine tert butyl ester,;

(c') methylating at 15° C.-30° C., for 4–24 hours the product obtained in step (a') or (b') with methyl iodide in an organic solvent selected from acetone and methyl ethyl ketone;

(d') removing the N-carboterbutoxy group of the aminoacid and the tert-butyl radical in an acid environment, using trifluoroacetic acid or gaseous HCl solution in an inert solvent selected from chloroform and methylene chloride; and (e') substituting the $X^-$ anion for the $I^-$ anion eluting an aqueous or alcoholic solution of the product of step (d') on a weakly basic ion exchange resin.

6. L-N-carboterbutoxy aminoacyl L-norcarnitine tert-butyl ester wherein said aminoacyl group comprises $$I-COCH-R$$
$$\phantom{I-COCH-}|$$
$$\phantom{I-COCH-}NH_2$$

and R is an alkyl radical selected from the group consisting of 1-methylpropyl, isobutyl, isopropyl, mercaptomethyl, and 3-guanidinopropyl and their pharmacologically acceptable salts.

7. L-N-carbotertbutoxy aminoacyl L-norcarnitine tert-butyl ester of claim 6 of the formula

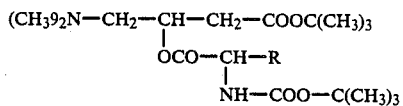

wherein R is an alkyl radical selected from the group consisting of 1-methyl-propyl, isobutyl, isopropyl, mercaptomethyl and 3-guanidinopropyl, and their pharmacologically acceptable salts.

8. A pharmaceutical composition having hepatoprotecting activity comprising an effective amount of a compound of the formula (1)

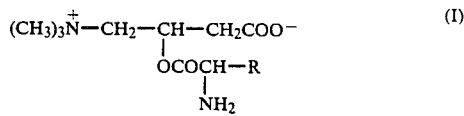

wherein R is an alkyl radical selected from the group consisting of mercaptomethyl and 3-guanidinopropyl, and their pharmacologically acceptable salts, and a pharmaceutically acceptable carrier.

9. The process, as in claim 5 wherein the separation of step (b') is carried out by chromatography on a silica column or by preparative HPLC.

10. The process as in claim 4 wherein the weakly basic resin of step (b) is a resin which is a macroreticular weakly basic resin which has a styrene divinyl benzene polymer backbone and a tertiary amine functionality.

11. The salt as in claim 1, comprising L-cysteinyl L-carnitine chloride hydrochloride.

12. The salt as in claim 1, comprising L-arginyl L-carnitine chloride hydrochloride.

* * * * *